United States Patent
Lambert

(10) Patent No.: US 6,772,758 B2
(45) Date of Patent: Aug. 10, 2004

(54) BREATHING PROTECTOR

(75) Inventor: Hans Lambert, Stockholm (SE)

(73) Assignee: Atos Medical, Horby (SE)

( * ) Notice: Subject to any disclaimer, the term of this patent is extended or adjusted under 35 U.S.C. 154(b) by 37 days.

(21) Appl. No.: 10/108,822

(22) Filed: Jul. 30, 2002

(65) Prior Publication Data

US 2003/0029456 A1 Feb. 13, 2003

Related U.S. Application Data

(63) Continuation-in-part of application No. 09/355,131, filed on Sep. 30, 1999, now abandoned.

(51) Int. Cl.[7] .............................................. A61M 16/00
(52) U.S. Cl. ........................... 128/204.17; 128/207.14; 128/200.26; 128/201.13
(58) Field of Search ....................... 128/200.26, 207.14, 128/207.16, 207.29, 201.13, 205.27, 204.17; 623/9; 606/108

(56) References Cited

U.S. PATENT DOCUMENTS

| | | | | |
|---|---|---|---|---|
| 4,325,366 A | * | 4/1982 | Tabor .................... | 128/207.16 |
| 4,538,607 A | * | 9/1985 | Saul ...................... | 128/207.16 |
| 4,582,058 A | * | 4/1986 | Depel et al. ........... | 128/207.17 |
| 4,971,054 A | * | 11/1990 | Andersson et al. .... | 128/207.16 |
| 5,022,394 A | * | 6/1991 | Chmielinski ........... | 128/207.14 |
| 5,042,468 A | * | 8/1991 | Lambert ................. | 128/200.26 |
| 5,201,309 A | * | 4/1993 | Friberg et al. ......... | 128/207.14 |
| 5,738,095 A | * | 4/1998 | Persson ................. | 128/207.14 |
| 5,848,590 A | * | 12/1998 | Smith ..................... | 128/201.13 |
| 6,422,235 B1 | * | 7/2002 | Persson ................. | 128/200.26 |

FOREIGN PATENT DOCUMENTS

WO     WO 91/05579     * 5/1991

* cited by examiner

*Primary Examiner*—Mital Patel
(74) *Attorney, Agent, or Firm*—James Ray & Associates

(57) ABSTRACT

A breathing protector for a laryngectomized or tracheotemized person to be applied over a tracheostoma includes a heat-moisture exchanger body which communicates with the tracheostoma through an inlet (relative to exhaling) and has contact surface turned toward the person. A substantially flat surface layer on the body faces the neck when the breathing protector is applied to the neck covering the stoma and is dimensioned to extend beyond the stoma to cover also a part of the neck surrounding the stoma. A elate covers a flat end surface on the heat-moisture exchanger body which is sandwiched between the surface layer and the plate. An outlet opening extends along the periphery of the heat-moisture exchanger body between the surface layer and the plate to impart to respiration air at least one component which is substantially parallel with the surface layer.

12 Claims, 2 Drawing Sheets

BREATHING PROTECTOR

CROSS REFERENCE TO RELATED APPLICATIONS

The present application is a continuation-in-part of pending prior application Ser. No. 09/355,131, filed Sep. 30, 1999, now abandoned entitled "Breathing Protector".

BACKGROUND OF THE INVENTION

1. Field of the Invention

The present invention relates to a breathing protector for a laryngectomized or tracheotomized person with a stoma communicating with trachea, to be applied to the person's neck covering the stoma. The person breathes fully or partially through the protector in order that moisture and heat shall be exchanged between exhaled air and inhaled air.

More particularly the invention relates to a breathing protector of the kind comprising a first opening for communication with the stoma; a second opening for communication with the surroundings; a flow path for respiration air between said first and second openings, and a heat-moisture exchanger body in said flow path.

2. Description of the Related Art

Protectors of the kind referred to are described in U.S. Pat. No. 3,920,009 (Olsen) and in U.S. Pat. No. 5,022,394 (Chemielinski). The devices disclosed therein function well as a heat-moisture exchanger the respiration air following a straight flow path through the exchanger body between the first and second openings. However, these prior art protectors are disadvantageous as said second opening communicating with the surroundings can easily be covered by a shirt, scarf, or the like, and when this happens, the flow of respiration air through the stoma will be obstructed, causing difficulty in breathing.

A breathing protector of the kind referred to herein which attempts to alleviate this problem is described in WO 95/17138 (Persson). The respiration air also in this case follows a straight path through the exchanger body between the first and second openings. The protector includes a movable spring biased cover plate that can be depressed against the surface of the heat-moisture exchanger body at said second opening to shut off the flow of air through said body, the respiration air then passes through a voice prosthesis located in the wall between trachea and esophagus of the user. When the cover plate valve is not depressed, the respiration air flows through the breathing protector at right angles to the said straight path through the exchanger body at said second opening. The device therefore can be worn beneath, for example, a shirt without the flow of air to and from the user being obstructed. However, this prior art breathing protector has the disadvantage of being of a relatively complicated structure and being relatively expensive to manufacture due to the complexity thereof. Moreover, the prior art breathing protector has a relatively large axial length.

SE-B-348 643 (Gibeck), GB-A-2 214 089 (Andersson et al), and GB-A-2 250 201 (Andersson et al) disclose breathing protectors of the kind referred to herein which at said second opening are provided with an element that deflects, in a transverse direction, the respiration air flowing along the straight path through the heat-moisture exchanger body, but also these breathing protectors suffer from disadvantages similar to those of the breathing protector disclosed in WO 95/17138.

BRIEF SUMMARY OF THE INVENTION

The primary object of the present invention is to provide a breathing protector which eliminates the risk of blocking of the flow of air and which is simultaneously of a very simple and reliable construction.

To achieve this object the invention provides a breathing protector of the kind referred to herein further comprising a substantially flat surface formed by said body and facing the neck when the breathing protector is applied to the neck covering the stoma, said substantially flat surface being dimensioned to extend beyond the stoma to cover also a part of the neck surrounding the stoma, said second opening including at least one part a direction of which has at least one component which is substantially parallel with said substantially flat surface.

By this arrangement which does not increase the overall length of the breathing protector it is possible for the respiration air to flow through the breathing protector even if a shirt or the like covers the outer end, of the protector.

In a preferred embodiment all of said second opening has a direction which is substantially parallel with said substantially parallel with said substantially flat surface, making certain that none of the flowing air will be affected by any clothing that comes into contact with the breathing protector.

This embodiment can be accomplished in a simple way by providing on the heat-moisture exchanger body a flat end surface that is turned away from said substantially flat surface, and a plate covering the end surface. The plate also supports the heat-moisture exchanger body and prevents it from being contaminated by clothing that contacts the outside of the body.

Preferably, said second opening is fully open around the entire periphery of the heat-moisture exchanger body, thereby providing maximum usage of the available space and permitting the design of the breathing protector to be simplified as much as possible, thus making it simple and inexpensive to manufacture and simple for the patient to handle.

In certain cases, it may be appropriate to arrange a casing that houses the heat-moisture exchanger body. An opening is made in the casing for said at least one part of said second opening. The heat-moisture exchanger body will thus be better protected against external effects.

The breathing protector can comprise an attachment device for attaching the breathing protector to the skin of the person, and heat-moisture exchanger body can be removably attached to the attachment device. This is advantageous in that the heat-moisture exchanger body can be replaced without loosening the connection with the skin of the person. This makes the use of the breathing protector considerably more comfortable because loosening this connection can cause irritation and pain, especially if the attachment device comprises an attachment device. It is preferred that the connection between the heat-moisture exchanger body and the attachment film comprises an adhesive. This provides a design which is very simple as compared with some form of locking or snap-in device, thereby reducing manufacturing costs and making it very easy to replace the heat-moisture exchanger body.

In accordance with another preferred embodiment the heat-moisture exchanger body has an open structure with several flow passages randomly oriented therein, for example as in wadding or foamed plastic.

The breathing protector can have a valve function for shutting off or throttling air flow through said flow path. The heat-moisture exchanger body in that case is elastic in at least one direction perpendicular to said substantially flat surface. A socket projects at substantially right angle from the substantially flat surface and communicates with said first opening, the heat-moisture exchanger body forming a through hole in register with said first opening and receiving the socket therein. The socket extends over part of the length of the hole, and the plate which can be engaged with an annular end surface of the socket under compression of the heat-moisture exchanger body against the substantially flat surface, corresponding to a closed condition of the valve function, the heat-moisture exchanger body biasing the plate to a position spaced from said annular end surface, corresponding to an open condition of the valve function.

The invention will be explained in more detail with reference to the accompanying drawings.

BRIEF DESCRIPTION OF THE DRAWINGS

In the drawings illustrating preferred embodiments of the invention

DETAILED DESCRIPTION OF THE INVENTION

Figure 1:
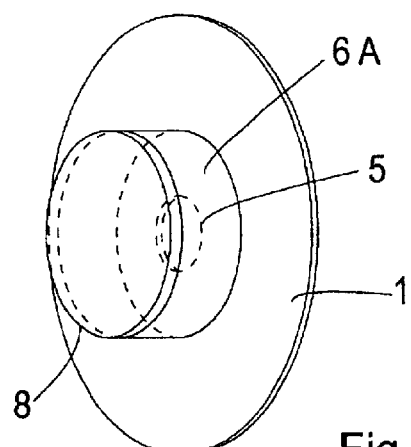
FIG. 1 is a perspective view of a first embodiment of the breathing protector in accordance with the invention.
Figure 2:
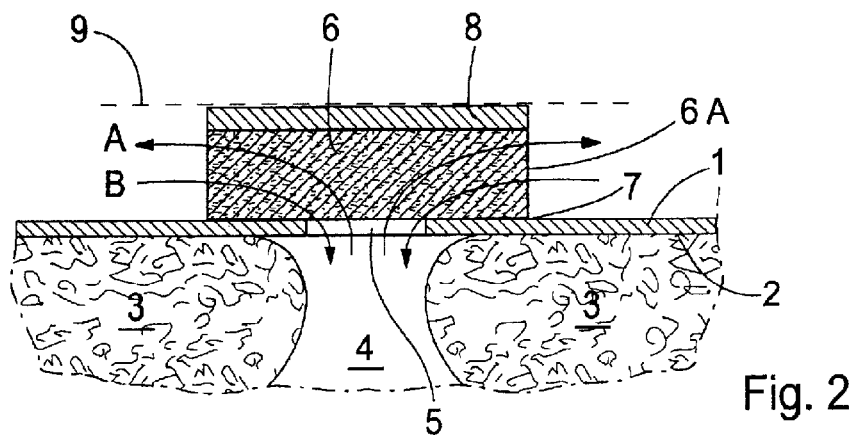
FIG. 2 is an axial cross sectional view of the breathing protector in FIG. 1.
Figure 3:
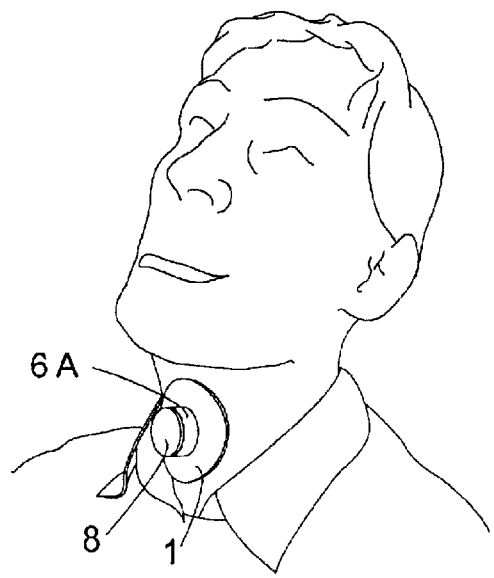
FIG. 3 is a perspective view illustrating the mounting of the breathing protector in FIGS. 1 and 2 on a person's neck.

The embodiment of the breathing protector shown in FIGS. 1 to 3 comprises an attachment device for attaching the breathing protector to the neck of a person having a tracheostoma 4 communicating with the person's trachea. The attachment device is an adhesive tape comprising a film 1 having an adhesive layer 2 on one side thereof to be applied to the person's neck. The film adheres to skin sections 3 which are located around stoma 4 and forms a through opening 5 located directly opposite stoma 4.

A substantially circular-cylindrical heat-moisture exchanger body 6 having two flat end surfaces and a cylindrically curved surface 6A has a layer 7 of adhesive on the end surface thereof that is intended to face the neck. The adhesive layer 7 covers an annular area around a central circular area which is not covered by adhesive and is intended to be located directly opposite the tracheostoma 4 and the opening 5 in the adhesive film 1 forming the attachment device. The adhesive layer 7 before use thereof is provided with a protective film that covers the adhesive layer. After removal of the protective film the heat-moisture exchanger body is attached to the outside of the adhesive film 1 by pressing the adhesive layer 7 against the film 1. At the outer end surface of the heat-moisture exchanger body 6, a cover plate 8 is attached which can be made of hard or soft material and preferably consists of a soft elastic plastic material. Thus, the heat-moisture exchanger body 6 is sandwiched between the film 1 and the cover plate 8 in an air flow path extending between the opening 5 and the opening formed between the film 1 and the cover plate 8 around the curved outside surface 6A of the heat-moisture exchanger body 6. The surface 6A is exposed to the surroundings.

Arrows A and B illustrate the flow path for the respiration air through the heat-moisture exchanger body at exhaling and inhaling, respectively. As shown, the air flow through the opening 5 is an axial air flow which is deflected at a right angle providing a flow that is substantially radial at the opening surrounding the curved surface 6A of the heat-moisture exchanger body 6. As shown in FIG. 2, a piece of clothing indicated by a broken line 9, which contacts the outside of the breathing protector will not in any way prevent flow through the heat-moisture exchanger body 6.

The material of the heat-moisture exchanger body 6 is appropriately soft or elastic so that the breathing protector readily follows the contours of the skin without chafing and without leakage occurring between the film 1 and the skin. The material of the heat-moisture exchanger body should include flow passages therein and should have an open structure in which the flow passages are randomly oriented. The material can comprise, for example, paper, foamed plastic, wadding made of different fibers, or combinations thereof. It can also be impregnated with a moisture absorbing substance. It is advantageous if the pores or interstices in the material do not have any special direction so that the breathing air can easily pass through the material in a number of directions in order to achieve the intended deflection.

The breathing protector illustrated in FIG. 1 is an optimal embodiment which can be easily manufactured and handled.

Figure 4:
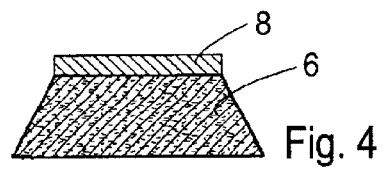
FIGS. 4 and 5 are axial cross sectional views of modified embodiments of the heat-moisture exchanger body.
Figure 5:
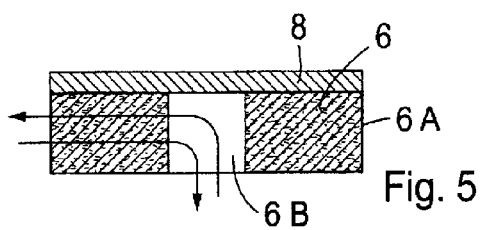

The heat-moisture exchanger body 6 can have a shape that differs from that in the embodiment according to FIGS. 1–3. It can, for example, be a truncated cone as shown in FIG. 4, or a cylinder with a central hole 6B as shown in FIG. 5, and it does not of course have to be circular.

Figure 6:
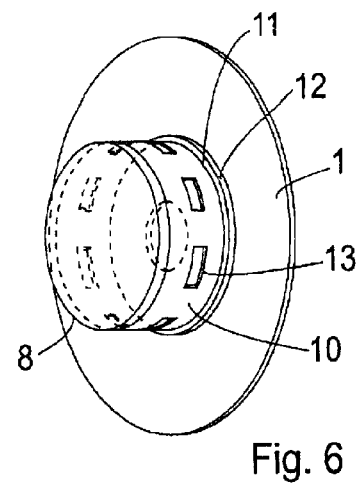
FIG. 6 is a perspective view of a second embodiment of the breathing protector of the invention.
Figure 7:
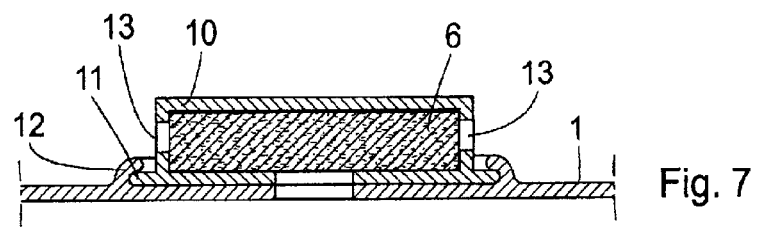
FIG. 7 is an axial cross sectional view of the breathing protector in FIG. 6, and FIGS. 8 and 9 are axial cross sectional views of a third embodiment of the breathing protector of the invention with a valve function, showing the valve open and closed, respectively.

If a more protected heat-moisture exchanger body is desired by sacrificing a certain amount of simplicity and reducing to some extent the area of said second opening, it can be housed in casing 10 as shown in FIGS. 6 ad 7. As an alternative to having the heat-moisture exchanger body attached directly to the attachment film 1, the heat-moisture exchanger body can adhere to film 1 via casing 10. In that case casing 10 can be provided with a locking device such as a snap-in flange 11 on casing 10 designed to interact with a snap-on collar 12 on film 1. Casing 10 is provided with radially oriented openings 13 around its periphery. Openings 13 are relatively large so that the casing resembles a cage.

Figure 8:
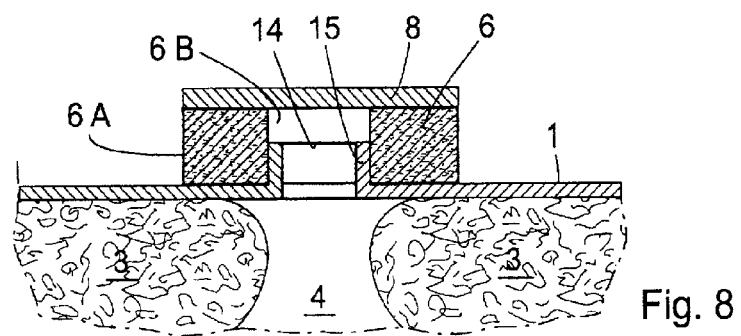
Figure 9:
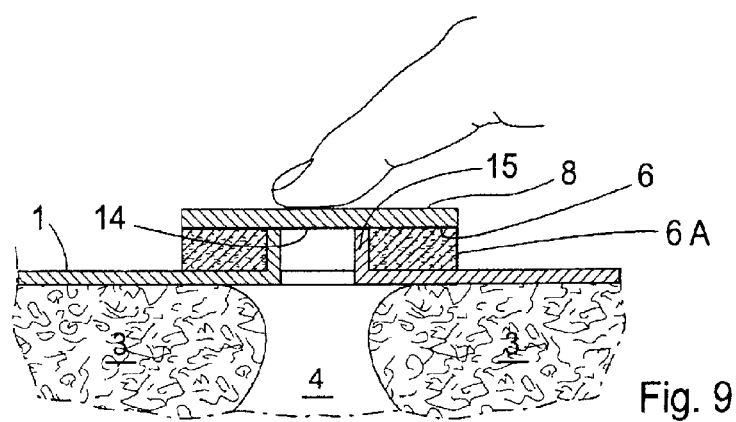

FIGS. 8 and 9 show an embodiment in which the breathing protector also incorporates a valve function so that the flow path through the breathing protector can be occluded when speech is to be produce by exhalation air being pressed through a voice prosthesis. It is an important embodiment of the invention since it was possible to integrate the valve function with the breathing protector without the breathing protector becoming significantly more complicated. In this case the heat-moisture exchanger body 6, just as in the embodiment shown in FIG. 5 is designed as a cylinder with a central through hole 6B. The heat-moisture exchanger body at its outer end is covered by plate 8. Tape 1 is provided with an outwardly oriented axial socket 15 that surrounds the opening 5 in the tape and projects into the central hole 6B over part of the length thereof. The heat-moisture exchanger body in this case should be made of a relatively soft elastic material. The valve is closed by exerting finger pressure against the outside of plate 8, FIG. 9, and compressing the heat-moisture exchanger body until the inside surface of plate 8 contacts the annular end surface 14 of socket 15 in hole 6B. This makes it impossible for air to pass through the breathing protector.

Socket 15 can either be attached to plate 8 and oriented inwards or replaced by a circular band that contacts the wall surface of the hole. Alternatively, socket 15 or, in applicable cases, the circular band can be placed on the outer curved surface 6A of the heat-moisture exchanger body.

What is claimed is:

1. A breathing protector for a laryngectomized or tracheotomized person with a stoma communicating with trachea, to be applied to the person's neck covering the stoma, said breathing protector comprising:

a first opening for communication with the stoma;

a second opening for communication with the surroundings;

a flow path for respiration air between said first and second openings;

a heat-moisture exchanger body in said flow path;

a substantially flat surface layer on said body facing the neck when the breathing protector is applied to the neck covering the stoma, said substantially flat surface layer being dimensioned to extend beyond the stoma to cover also a part of the neck surrounding the stoma, and a plate covering a flat end surface on the heat-moisture exchanger body which is sandwiched between said substantially flat surface layer and said plate, said second opening extending along at least a part of a periphery of the heat-moisture exchanger body to impart to respiration air at least one component which is substantially parallel with the substantially flat surface layer.

2. The breathing protector in accordance with claim 1 wherein all of said second opening has a direction which is substantially parallel with said substantially flat surface layer.

3. The breathing protector in accordance with claim 1 wherein the heat-moisture exchanger body has a circular-cylindrical shape, and wherein at least part of said second opening has a radial orientation.

4. The breathing protector in accordance with claim 3 wherein all of said second opening has said radial orientation.

5. The breathing protector in accordance with claim 1 wherein said second opening is fully open around an entire periphery of the heat-moisture exchanger body.

6. The breathing protector in accordance with claim 1 further comprising a casing in which the heat-moisture exchanger body is housed.

7. The breathing protector in accordance with claim 1 further comprising an attachment device for attaching the breathing protector to the skin of the person.

8. The breathing protector in accordance with claim 7 wherein the heat-moisture exchanger body is removably attached to said attachment device.

9. The breathing protector in accordance with claim 7 wherein said attachment device comprises an attachment film and wherein the heat-moisture exchanger body is removably attached to said attachment film.

10. The breathing protector in accordance with claim 9 wherein the heat-moisture exchanger body is removably attached to the attachment film by means of an adhesive.

11. The breathing protector in accordance with claim 1 wherein the heat-moisture exchanger body includes several flow passages therein and wherein said heat-moisture exchanger body has an open structure in which said flow paths are randomly oriented.

12. The breathing protector in accordance with claim 1 including a valve function for shutting off or throttling air flow through said flow path, the heat-moisture exchanger body being elastic in at least one direction perpendicular to said substantially flat surface, the breathing protector further comprising a socket projecting at substantially a right angle from said substantially flat surface and communicating with said first opening, the heat-moisture exchanger body forming a through hole in register with said first opening and receiving said socket therein, the socket extending over part of a length of the hole, the plate being engaged with an annular end surface of said socket, under compression of the heat-moisture exchanger body against the substantially flat surface, corresponding to a closed condition of the valve function, the heat-moisture exchanger body biasing the plate to a position spaced from said annular end surface, corresponding to an open condition of the valve function.

* * * * *